United States Patent [19]

Niewohner et al.

[11] Patent Number: 4,921,998

[45] Date of Patent: May 1, 1990

[54] SUBSTITUTED AMINO-5,6,7,8-TETRAHYDRONAPHTHYL-OXYACETIC ACIDS, PROCESSES FOR THEIR PREPARATION AND THEIR USE AS MEDICAMENTS

[75] Inventors: Ulrich Niewohner, Wermelskirchen; Franz-Peter Hoever, Cologne; Bodo Junge, Wuppertal; Elisabeth Perzborn, Wuppertal; Friedel Seuter, Wuppertal; Volker-Bernd Fiedler, Leverkusen, all of Fed. Rep. of Germany

[73] Assignee: Bayer Aktiengesellschaft, Leverkusen, Fed. Rep. of Germany

[21] Appl. No.: 352,073

[22] Filed: May 15, 1989

Related U.S. Application Data

[62] Division of Ser. No. 68,002, Jun. 29, 1987.

[30] Foreign Application Priority Data

Jul. 16, 1986 [DE] Fed. Rep. of Germany ....... 3623941

[51] Int. Cl.$^5$ ........................................ C07C 101/72
[52] U.S. Cl. ....................... 560/45; 562/452; 564/167
[58] Field of Search ........................ 560/45; 562/452; 564/167

[56] References Cited

U.S. PATENT DOCUMENTS

| | | | |
|---|---|---|---|
| 3,829,467 | 8/1974 | Diamond et al. | 560/45 |
| 4,035,512 | 7/1977 | Sugihara et al. | 560/45 |
| 4,214,093 | 7/1980 | Fujii et al. | 560/45 |
| 4,410,519 | 10/1983 | Seiler et al. | 564/167 |
| 4,559,361 | 12/1985 | Oka | 564/167 |
| 4,707,497 | 11/1987 | Cecchi et al. | 562/452 |

*Primary Examiner*—Bruce D. Gray
*Attorney, Agent, or Firm*—Sprung Horn Kramer & Woods

[57] ABSTRACT

Antithrombotic, antiatherosclerotic and antiischaemic compounds of the formula

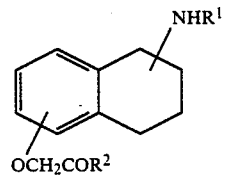

in which
$R^1$ is

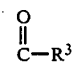

or $SO_2R^4$,
$R^3$ is aryl, substituted aryl, heteroaryl, aralkyl or the group

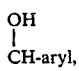

$R^4$ is aryl or substituted aryl,
$R^2$ is OH, alkoxy, phenoxy, benzoxy or $NR^5R^6$, and
$R^5$ and $R^6$ each independently is hydrogen or alkyl, or one of the radicals $R^5$ or $R^6$ is benzyl, and physiologically acceptable salts thereof with mono- and divalent cations.

1 Claim, No Drawings

SUBSTITUTED AMINO-5,6,7,8-TETRAHYDRONAPHTHYL-OXYACETIC ACIDS, PROCESSES FOR THEIR PREPARATION AND THEIR USE AS MEDICAMENTS

This is a division of application Ser. No. 68,002, filed Jun. 29, 1987, now allowed.

The present invention relates to new amino-5,6,7,8-tetrahydronaphthyl-oxyacetic acids, processes for their preparation and the use of amino-5,6,7,8-tetrahydronaphthyl-oxyacetic acids as medicaments, in particular as antithrombotics, antiatherosclerotics and antiischaemic agents.

Thrombosis and arteriosclerotic vascular changes are controlled, above all, by the interaction of two metabolites of arachidonic acid, that is to say by thromboxan $A_2$ ($TXA_2$) and by prostacyclin ($PGI_2$). $TXA_2$ has an aggregating effect on blood platelets, and $PGI_2$ has an antiaggregating effect. Moreover, $TXA_2$ has a vasoconstrictory effect and $PGI_2$ a vasodilatory effect.

In a number of thrombo-embolic and ischaemic diseases, hyperaggregability of the platelets or an increased platelet consumption leads to an increased thromboxan synthesis, so that the $TXA_2$ and $PGI_2$ equilibrium is disturbed. It is therefore desirable for the therapy and propylaxis of thrombo-embolic and ischaemic diseases for the thromboxan effect to be inhibited and the protective properties of the $PGI_2$ therefore to be increased.

It has now been found, surprisingly, that certain amino-5,6,7,8-tetrahydronaphthyloxyacetic acids have a specific and potent antagonistic action in respect of thromboxan $A_2$.

Thromboxan-antagonistic and platelet aggregation-inhibiting amino-5,6,7,8-tetrahydronaphthyloxyacetic acids of the general formula (I)

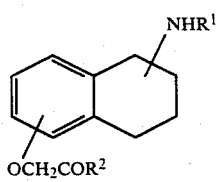

in which
$R^1$ represents

or $SO_2R^4$
wherein
$R^3$ represents aryl, substituted aryl, heteroaryl, aralkyl or the group

and wherein
$R^4$ represents aryl or substituted aryl, and
$R^2$ represents OH, alkoxy, phenoxy, benzoxy or $NR^5R^6$,
wherein
$R^5$ and $R^6$ are identical or different and each represents hydrogen or alkyl, or
one of the radicals $R^5$ or $R^6$ represents benzyl, and physiologically acceptable salts thereof with mono-or divalent cations have been found.

Compounds of the general formula (I) which are of particular interest are those in which
$R^1$ represents $CO-R^3$ or $SO_2R^4$,
wherein
$R^3$ represents phenyl or naphthyl which optionally carries 1, 2 or 3 identical or different substituents from the group comprising halogen, cyano, trifluoromethyl and alkyl with 1 to 4 C atoms, or represents pyridine, quinoline or aralkyl with 7 to 12 carbon atoms, the aralkyl radical optionally being substituted in the alkyl part by halogen or hydroxyl and optionally being substituted in the aryl part by halogen or alkyl with 1 to 4 carbon atoms, or represents the group CHOH-aryl,
wherein
aryl denotes phenyl or naphthyl which is optionally substituted by 1, 2 or 3 radicals from the group comprising halogen, cyano, trifluoromethyl and alkyl with 1 to 4 carbon atoms, $R^4$ represents phenyl or naphthyl, which optionally carry 1, 2 or 3 identical or different substituents from the group comprising halogen, cyano, trifluoromethyl and alkyl with 1 to 4 C atoms, and $R^2$ represents hydroxyl, phenoxy, benzoxy or alkoxy with 1 to 4 carbon atoms, or represents the group $NR^5R^6$,
wherein
$R^5$ and $R^6$ are identical or different and each represent hydrogen or alkyl with 1 to 4 carbon atoms, or one of the radicals $R^5$ or $R^6$ represents benzyl,
and physiologically acceptable salts thereof with mono- or divalent cations.

Fluorine and chlorine are of particular interest from the group of halogens.

The new amino-5,6,7,8-tetrahydronaphthalene-oxyacetic acid derivatives of the formula (I) can exist both as enantiomers and enantiomer pairs, and if a further asymmetry is present in one of the radicals, as diastereomer pairs.

Preferred processes for preparing optical isomers are: making diastereomeric salts of amines of formula II with optical active acids, separation of the diastereomeric salts by crystallisation and following isolation of the free optical active amines, or via the preparation of optical active imines of ketones of formula V with (+) or (−) α-methylbenzylamines, subsequent hydration of the imine-double-bond and removal of the benzylmoiety by further hydration.

It has furthermore been found that the amino-5,6,7,8-tetrahydronaphthyl-oxyacetic acids I are obtained by a process in which the amines of the general formula (II)

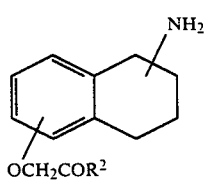

in which
$R^2$ has the abovementioned meaning, are reacted with carboxylic acids of the general formula $R^3$-COOH, R³ having the abovementioned meaning, or activated derivatives thereof, such as acid chlorides or anhydrides or activated esters, or with sulphonic acids of the general formula R⁴SO₃H, R⁴ having the abovementioned meaning, or activated derivatives thereof, such as acid chlorides or activated esters, in a manner which is known per se. In the case where R² = OH, the reaction is followed by hydrolysis to give the free carboxylic acids.

It has furthermore been found that the amino-5,6,7,8-tetrahydronaphthyl-oxyacetic acid derivatives I are also obtained by a process in which the phenols of the general formula (III)

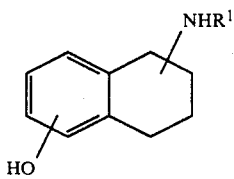

in which
R¹ has the abovementioned meaning, are reacted with acetic acid derivatives of the general formula (IV)

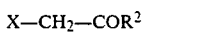

in which
X denotes a leaving group, such as, for example, Cl, Br, I, SO₂CH₃ or

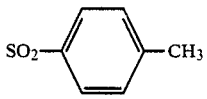

and
R² has the abovementioned meaning, in the presence of acid-binding agents.

This process variant is particularly suitable if R¹ contains no sulphur atom.

In the case where R² ≠ OH, the reaction is followed by hydrolysis to give the free carboxylic acids.

The aminotetralin-oxyacetic acid derivatives II are obtained from the corresponding tetralones V

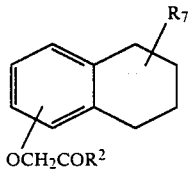

wherein
R₇ is a·keto group and
R² has the abovementioned meaning, by reductive amination by a process analogous to those known from the literature (for example J. Am. Chem. Soc. 93, 2897 (1971); Rylander, "Catalytic Hydrogenation", pages 291–303, Academic Press, Inc., N.Y., 1967; and Org.-Reactions 4, 174–255 (1948)).

The tetralones V are obtained by alkylation of the corresponding hydroxytetralins VI

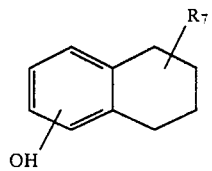

in which
R₇ has the abovementioned meaning, with acetic acid derivatives of the general formula X—CH₂—CO₂R² (IV), in which X and R² have the abovementioned meaning, by processes which are known from the literature (for example Patai "The Chemistry of the Hydroxyl group", part 1, pages 454–466, Interscience Publishers, N.Y., 1971; and Tetrahedron 30, 1379 (1974)).

The hydroxytetralones VI are known from the literature in some cases (for example J. Org. Chem. 14, page 366 (1949)), and some of them can be prepared from the known methoxytetralones XI by ether cleavage by a process analogous to those known from the literature (for example Org. Syntheses, Volume 51, page 109; and J. Chem. Soc. 1855 (1949)).

The aminotetralin-oxyacetic acid derivatives II can likewise be obtained by a process in which the acetamides VII

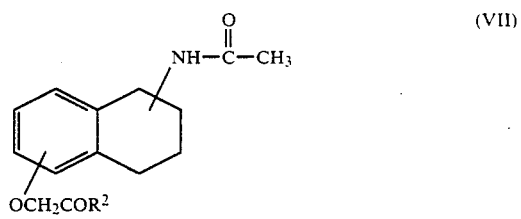

in which
R² has the abovementioned meaning, are subjected to acid or basic hydrolysis in a known manner. VII can be obtained in a manner analogous to that already described for III ·> II, by alkylation of the OH group of the phenols VIII

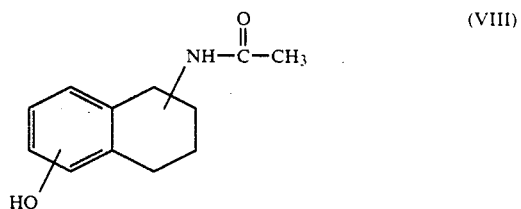

with the acetic acid derivatives IV. The acetylated amino-hydroxytetralins VIII are obtained from the corresponding amino-hydroxytetralins IX

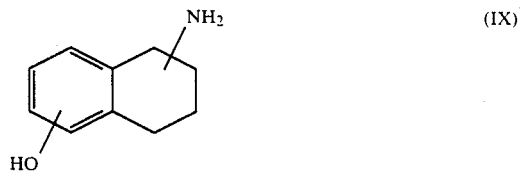

or salts thereof with inorganic acids, by acetylation of the amino and hydroxyl function and subsequent selective hydrolysis of the ester by generally known processes.

The phenols of the general formula III can also be prepared from the aminohydroxytetralins IX by processes analogous to those known from the literature (for example Chem. Ber. 103, 788 (1970)). This procedure is particularly suitable if $R^1$ does not contain a sulphur atom. The phenols of the general formula III can also be prepared from compounds of the general formula XII

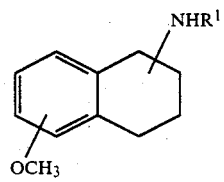

(XII)

by ether cleavage by known processes, for example by reaction with $BBr_3$.

The amino-hydroxy-tetralones IX are known in some cases (for example J. Med. Chem. 22, 1469 (1979)), or they can be prepared via the methoxy-aminotetralins X

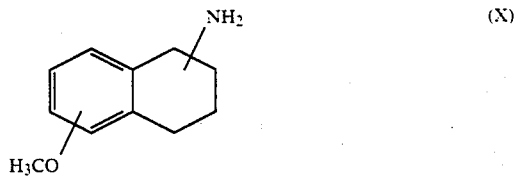

(X)

or salts thereof with inorganic acids, by reductive amination from the corresponding known methoxy-tetralones XI

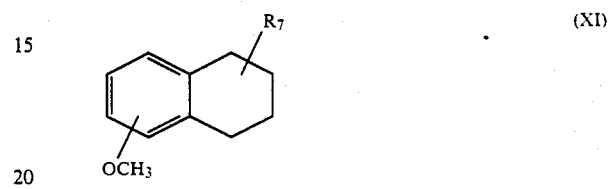

(XI)

in which
  $R^7$ has the abovementioned meaning, by processes analogous to known processes.

Examples which may be mentioned of the methoxytetralones XI used as starting substances are: 5-methoxy-1-tetralone, 5-methoxy-2-tetralone, 6-methoxy-1-tetralone, 6-methoxy-2-tetralone and 6-methoxy-3-tetralone.

The syntheses sequences can be summarized in reaction scheme as follows, starting from the methoxy-tetralones XI:

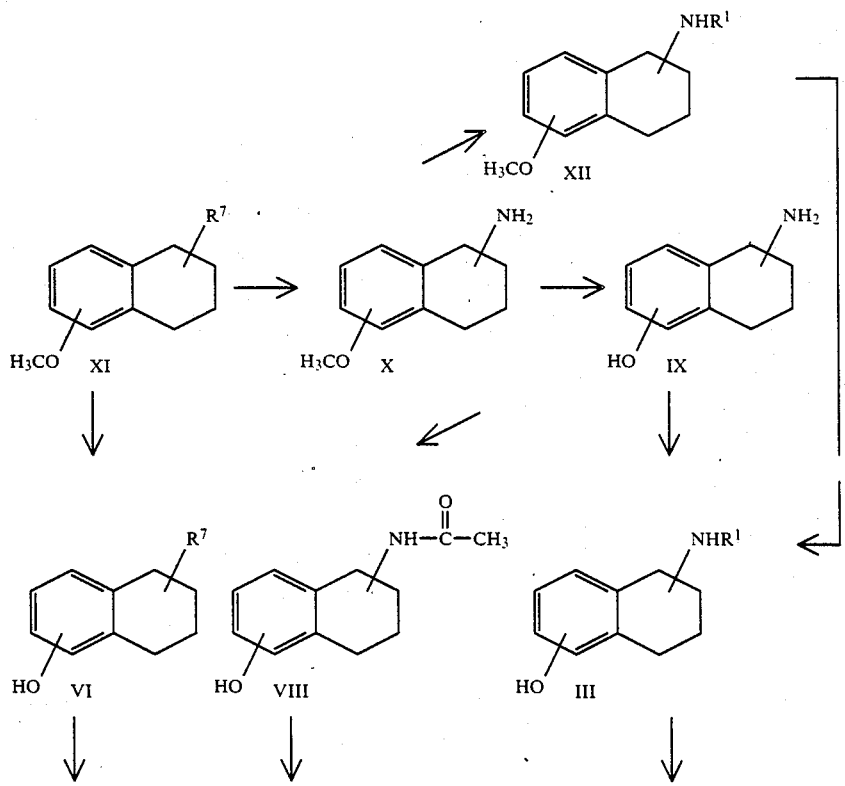

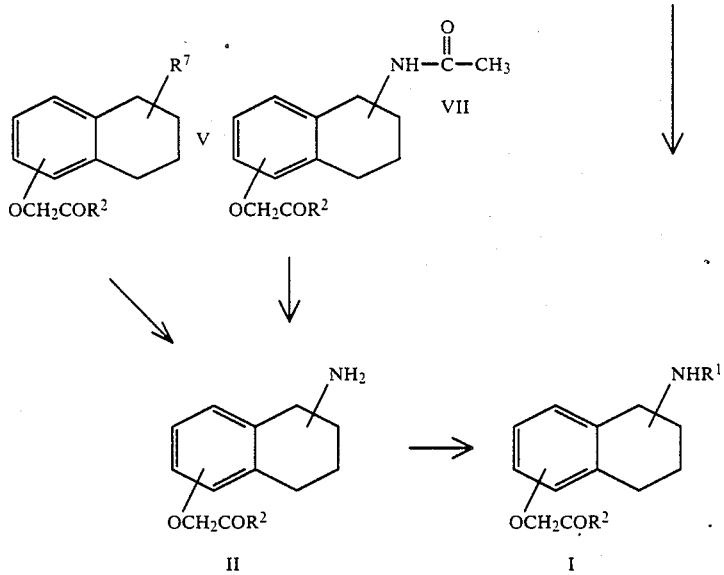

wherein
R¹, R² and R⁷ have the abovementioned meanings.
In the case where R¹=

R³ having the abovementioned meaning, the end products I are obtained by a process in which the amines of the general formula II are reacted with the corresponding carboxylic acids R²—COOH or activated derivatives thereof, for example acid chlorides, acid anhydrides or activated esters.

If the activated derivatives are employed, the reaction is advantageously carried out in the presence of an acid-binding agent, such as, for example, alkali metal hydroxides or carbonates or alkaline earth metal hydroxides or carbonates or organic bases, such as triethylamine, pyridine or N-ethylmorpholine.

Suitable solvents, depending on the nature of the carboxylix acid derivative employed, are organic solvents, such as, for example, methylene chloride, chloroform, ethyl acetate, tetrahydrofuran, ether or dimethylformamide, or protic solvents, such as, for example, water, methanol or ethanol.

The reaction temperature is between 0° and 100° C., preferably between 0° and 30° C.

If the free carboxylic acids R³—COOH are employed, the reaction can be carried out, for example, in the manner described in Chem. Ber. 103, 788 (1970).

In the case where R¹=SO₂R⁴, R⁴ having the abovementioned meaning, the end products I are obtained by reacting the amines of the general formula II with the corresponding sulphonic acids R⁴SO₃H or activated derivatives thereof, such as, for example, sulphonic acid chlorides, sulphonic acid anhydrides or sulphonic acid esters, in the presence of an acid-binding agent, such as, for example, alkali metal hydroxides or carbonates or alkaline earth metal hydroxides or carbonates or organic bases, such as, for example, triethylamine, pyridine or N-ethylmorpholine.

Suitable diluents are the same as those which have already been mentioned for the reaction with the carboxylic acid derivatives. If R² in the compounds of the general formula I represents O-alkyl or NR⁵R⁶, the reaction can be followed by hydrolysis under basic or acid conditions in a generally known manner.

The compounds of the general formula I are also obtained by the process variant from the phenols III in which R¹ has the abovementioned meaning by a procedure in which the phenols III are alkylated with acetic acid derivatives of the general formula IV in which R² and X have the abovementioned meaning.

The alkylation is advantageously carried out in the presence of an acid-binding agent, such as, for example, alkali metal hydroxides or carbonates or alkaline earth metal hydroxides or carbonates or organic bases, such as, for example, triethylamine, pyridine or diazabicycloundecane, in organic solvents, such as acetone, butanone, dimethylformamide, dimethylsulphoxide, ethanol, dioxane or toluene.

It is frequently advantageous to add an alkali metal halide, such as, for example, sodium iodide or potassium iodide, and a water-binding agent, such as a 3Å molecular sieve.

The reaction temperature is between 50° and 150°, preferably between 50° and 80° C., depending on the solvent.

Examples which may be mentioned of the compounds of the general formula I are: 5-(4-fluorophenylsulphonylamino)-5,6,7,8-tetrahydro-naphth-1-yl-oxyacetic acid, 5-phenylsulphonylamino-5,6,7,8-tetrahydro-naphth-1-yl-oxyacetic acid, 5-(4-Methylphenylsulphonylamino)-5,6,7,8-tetrahydro-naphth-1-yl-oxyacetic acid, 5-(3,4-dichlorobenzoylamino)-5,6,7,8-tetrahydro-naphth-1-yl-oxyacetic acid, 5-(3,4-dichlorobenzoylamino)-5,6,7,8-tetrahydro-naphth-2-yl-oxyacetic acid, 5-(4-fluorophenylsulphonylamino)-5,6,7,8-tetrahydro-naphth-2-yl-oxyacetic acid, 5-phenylsulphonylamino-5,6,7,8-tetrahydro-naphth-2-yl-oxyacetic acid, 6-(3,4-dichlorobenzoylamino)-5,6,7,8-tetrahydro-naphth-1-yl-oxyacetic acid, 6-(4-fluorophenylsulphonylamino)-5,6,7,8-tetrahydro-naphth-1-yl-oxyacetic acid, 6-(4-chlorophenylsulphonylamino)-5,6,7,8-tetrahydro-naphth-2-yl-oxyacetic acid, 6-(4-fluorophenylsulphonylamino)-5,6,7,8-tetrahydro-naphth-2-yl-oxyacetic acid, 7-(4-fluorphenylsulphonyl)amino)-5,6,7,8-tetrahydro-naphth-2-yl-oxyacetic acid, 7-(4-chlorophenylsulphonylamino)-5,6,7,8-tetrahydronaphth-2-yl-oxyacetic acid, 7-(4-chlorophenylsulphonylamino)-5,6,7,8-tetrahydro-naphth-1-yl-oxyacetic acid, 5-(4-methylphenylsulphonylamino)-5,6,7,8-tetrahydro-naphth-2-yl-oxyacetic acid, 6-(4-methylphenylsulphonylamino)-5,6,7,8-tetrahydro-naphth-2-yl-oxyacetic acid, 5-(4-trifluoromethylphenylsulphonylamino)-5,6,7,8-tetrahydronaphth-2-yl-oxyacetic acid, 5-(4-cyanophenylsulphonylamino)-5,6,7,8-tetrahydro-naphth-2-yl-oxyacetic acid, 6-(4-trifluoromethylphenylsulphonylamino)-5,6,7,8-tetrahydro-naphth-2-yl-oxyacetic acid, 5-(4-cyanophenylsulphonylamino)-5,6,7,8-tetrahydro-naphth-1-yl-oxyacetic acid, 5-(4-trifluormethylphenylsulphonylamino)-5,6,7,8-tetrahydro-naphth-1-yl-oxyacetic acid, 6-(4-cyanophenylsulphonylamino)-5,6,7,8-tetrahydro-naphth-1-yl-oxyacetic acid, 6-(4-trifluormethylphenylsulphonylamino)-5,6,7,8-tetrahydro-naphth-1-yl-oxyacetic acid, 6-(4-methylphenylsulphonylamino)-5,6,7,8-tetrahydro-naphth-1-yl-oxyacetic acid, 6-(4-cyanophenylsulphonylamino)-5,6,7,8-tetrahydro-naphth-2-yl-oxyacetic acid.

Possible formulation forms are the customary galenical administration forms, for example creams, tablets, pills, capsules, suppositories, emulsions and infusion and injection solutions. These formulation forms are prepared by methods which are known per se, using customary auxiliaries and excipients.

The medicaments thus prepared are used as required, for example by local, parenteral or oral administration.

Formulations which contain the compounds according to the invention in concentrations of about 0.1 to 10% by weight are particularly suitable. Aqueous solutions, which if appropriate are buffered to a pH of 6 to 8, are particularly preferred.

The dosage of the substituted amino-5,6,7,8-tetrahydro-naphthyl-oxyacetic acid derivatives in the medicaments according to the invention is preferably in a range from 0.05 to 100 mg/kg, in particular 0.1 to 20 mg/kg of body weight.

The substituted amino-5,6,7,8-tetrahydronaphthyloxyyacetic acids contained in the medicaments according to the invention are used as thromboxan antagonists and platelet aggregation-inhibitors for preventing and treating thromboses, thromboembolisms and ischaemic diseases, and as antiasthmatics and as antiallergics.

METHOD

Platelet aggregation inhibition in vitro

Blood from healthy donors who have taken no medicament for at least 14 days is used for the in vitro determination of the platelet aggregation-inhibiting action. The blood is taken up in 3.8% strength sodium citrate solution. Platelet-rich plasma (PRP) is obtained by centrifugation at 150 g at room temperature for 20 minutes (Jürgens/Beller: Klinische Methoden der Blutgerinnungsanalyse (Clinical Methods of Blood Coagulation Analysis); Thieme Verlag, Stuttgart 1959). The platelet aggregation is determined by the turbidometric method (Born, G. V. R.: J. Physiol. 162, 67, 1962) in an aggregometer at 37° C. For this, PRP is incubated with the test substance at 37° C. and the aggregation is then induced by addition of a collagen suspension. For the in vitro experiments, the minimum effective active compound concentration (MEC) which inhibits platelet aggregation in the corresponding PRP samples is quoted.

Platelet aggregation inhibition ex vivo

For the ex vivo investigations, the active substance is administered orally to the animals in a tylose suspension. After 90 minutes, the animals are exsanguinated and the PRP is obtained by means of centrifugation. The aggregation inhibition is measured analogously to the method described for the in vitro experiments; however, there is no preincubation of the samples.

The results of the collagen-induced platelet aggregation of some examples are shown in the table.

| Example No. | Inhibition of platelet aggregation (in vitro) Limit concentration [mg/l] |
|---|---|
| 54 | 0.3–0.1 |
| 55 | 3–1 |
| 56 | 0.3–0.1 |
| 57 | 0.3–0.1 |
| 58 | 0.1–0.03 |
| 63 | 10–3 |
| 66 | 10–3 |

EXAMPLE 1

5-Amino-1-methoxy-5,6,7,8-tetrahydro-naphthalene hydrochloride 50 mmol of 5-methoxy-1-tetralone, 0.5 mol of $NH_4OAc$ and 35 mmol of $NaBH_3CN$ are stirred in 150 ml of absolute MeOH at room temperature for 24 hours. The mixture is acidified to pH 2 with concentrated HCl and evaporated, the residue is taken up in 50 ml of $H_2O$ and the mixture is extracted by shaking 2–3 x with ether. Any precipitates which arise are filtered off and combined with the $H_2O$ phase. The $H_2O$ phase is brought to pH 10 with solid KOH, saturated with NaCl and extracted by shaking 3 x with ethyl acetate. After drying with $Na_2SO_4$, the organic phase is evaporated, the residue is dissolved in ether and the product is precipitated as the hydrochloride by passing in HCl. Yield: 79%; melting point: 250° C.

The following compounds were prepared in an analogous manner:

EXAMPLE 2

5-Amino-2-methoxy-5,6,7,8-tetrahydro-naphthalene hydrochloride

Yield: 79% of theory; melting point: 262° C.

EXAMPLE 3

6-Amino-1-methoxy-5,6,7,8-tetrahydro-naphthalene hydrochloride

Yield: 62% of theory; melting point: 258° C.

EXAMPLE 4

6-Amino-2-methoxy-5,6,7,8-tetrahydro-naphthalene hydrochloride

Yield: 42% of theory; melting point: 239° C.

EXAMPLE 5

7-Amino-1-methoxy-5,6,7,8-tetrahydro-naphthalene hydrochloride

Yield: 61.4% of theory; melting point: 97° C.

EXAMPLE 6

5-Amino-1-hydroxy-5,6,7,8-tetrahydro-naphthalene hydrobromide 0.15 mol of 5-amino-1-methoxy-5,6,7,8-tetrahydronaphthalene hydrochloride is heated at a bath temperature of 125° C. in 75 ml of aqueous 48% strength HBr for 3 hours. The mixture is evaporated, the residue is dissolved in a little ethanol and the products are precipitated as the hydrobromides by addition of ether. Yield: 80% of theory; melting point: 152° C.

The following compounds were prepared in an analogous manner:

EXAMPLE 7

5-Amino-2-hydroxy-5,6,7,8-tetrahydro-naphthalene hydrobromide

Yield: 18% of theory.

EXAMPLE 8

6-Amino-1-hydroxy-5,6,7,8-tetrahydro-naphthalene hydrobromide

Yield: 72% of theory; melting point: 248° C.

EXAMPLE 9

6-Amino-2-hydroxy-5,6,7,8-tetrahydro-naphthalene hydrobromide

Yield: 84% of theory; melting point: 275° C.

EXAMPLE 10

7-Benzenesulphonylamino-1-methoxy-5,6,7,8-tetrahydronaphthalene 10.25 g (56 mmol) of 7-amino-1-methoxy-5,6,7,8-tetra-hydro-naphthalene are dissolved in 100 ml of analytical grade pyridine, 10.6 g (60 mmol) of benzenesulphonyl chloride are added dropwise at room temperature, exothermic reaction, subsequently stir at room temperature for 1 hour, reaction mixture concentrated in vacuo, residue purified over a silica gel column ($K_{60}$, mobile phase toluol:acetone 10:1).

Yield: 10.8 g (61% of theory)

Rf value ($K_{60}$ film) 0.75 (mobile phase: toluene:ethanol: triethylamine 10:3:1).

EXAMPLE 11

5-Benzoylamino-1-hydroxy-5,6,7,8-tetrahydro-naphthalene 50 mmol of benzoic acid and 50 mmol of 1-hydroxybenzotriazole (HOBT) are taken in 200 ml of absolute tetrahydrofuran at 0° C. 55 mmol of dicyclohexylcarbodiimide (DCC) are added under $N_2$ and the mixture is stirred at 0° C. for 1 hour and then at room temperature for 1 hour. 50 mmol of 5-amino-1-hydroxy-5,6,7,8-tetrahydro-naphthalene hydrobromide and 50 mmol of triethylamine are added to this solution and the mixture is stirred at room temperature for 6 hours.

The mixture is filtered, the residue is rinsed thoroughly with tetrahydrofuran and the filtrate is evaporated. The residue is taken up in ethyl acetate and washed once with saturated $NaHCO_3$ solution, once with 1N HCl, once with saturated $NaHCO_3$ solution and once with saturated NaCl solution. After drying over $Na_2SO_4$, the mixture is evaporated, the residue is dissolved in a little acetone, and after 1 hour in a refrigerator the residual dicyclohexylurea which has precipitated out is filtered off. The filtrate is evaporated and the residue is recrystallized from acetone by addition of petroleum ether. Yield: 53% of theory; melting point: 160° C.

The compounds summarized in Table 1 were prepared in an analogous manner:

TABLE 1

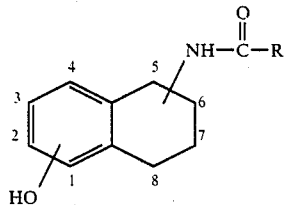

| | Substitution positions | | | % yield (in % of theory) | Melting point (in the case of crystals) or wave number of the amide band in the IR spectrum in the case of oils |
|---|---|---|---|---|---|
| Example | OH | NH—CO—R | Radical R | | |
| 12 | 1 | 5 | —CH(OH)—C₆H₅ | 76 | 1655 cm⁻¹ |
| 13 | 1 | 5 | pyridyl | 83 | 230° C. |
| 14 | 2 | 5 | phenyl | 31 | 1660 cm⁻¹ |

TABLE 1-continued

Structure: 2-acylamino-tetrahydronaphthalene with OH on ring, NH-CO-R substituent; positions numbered 1-8 (1=HO position shown).

| Example | Substitution positions OH | NH—CO—R | Radical R | % yield (in % of theory) | Melting point (in the case of crystals) or wave number of the amide band in the IR spectrum in the case of oils |
|---|---|---|---|---|---|
| 15 | 2 | 5 | -CH(OH)-phenyl | 27 | 1650 cm$^{-1}$ |
| 16 | 1 | 6 | phenyl | 60 | 198° C. |
| 17 | 1 | 6 | -CH(OH)-phenyl | 77 | 1660 cm$^{-1}$ |
| 18 | 1 | 6 | pyridyl | 58 | 232–33° C. |
| 19 | 2 | 6 | phenyl | 82 | 173–75° C. |
| 20 | 2 | 6 | -CH(OH)-phenyl | 58 | 1640 cm$^{-1}$ |
| 21 | 2 | 6 | pyridyl | 85 | 230° C. |

EXAMPLE 22

5-Acetylamino-1-hydroxy-5,6,7,8-tetrahydro-naphthalene 50 mmol of 5-amino-1-hydroxy-5,6,7,8-tetrahydronaphthalene are stirred in a solution of 200 mmol of acetic anhydride and 200 mmol of triethylamine, to which a spatula-tip of dimethylaminopyridine has been added, for 2 hours. The mixture is filtered, the residue is rinsed thoroughly with tetrahydrofuran and the filtrate is evaporated. The residue is taken up in ethyl acetate and the mixture is washed with 1N HCl, saturated NaHCO$_3$, 1N HCl, saturated NaHCO$_3$ and saturated NaCl solution, dried over Na$_2$SO$_4$ and evaporated. The bisacetate which remains is dissolved in 100 ml of MeOH and the solution is then added dropwise to 100 ml of 1N KOH at room temperature. The mixture is stirred at an internal temperature of 50° C. for 2 hours and acidified with concentrated HCl and the MeOH is stripped off. The acid aqueous phase is extracted by shaking 2 to 3 times with ethyl acetate and the combined organic phases are dried with Na$_2$SO$_4$ and evaporated. The residue is recrystallized from ethyl acetate.

Yield: 92% of theory $^1$H-NMR (CD$_3$OD): δ=1.95 (s, 3H)

The following compounds were prepared in an analogous manner:

EXAMPLE 23

5-Acetylamino-2-hydroxy-5,6,7,8-tetrahydro-naphthalene

Yield: 33% of theory $^1$H-NMR (CD$_3$OD): δ=2.0 (s, 3H)

EXAMPLE 24

6-Acetylamino-1-hydroxy-5,6,7,8-tetrahydro-naphthalene

Yield: 81% of theory $^1$H-NMR (CD$_3$OD): δ=1.95 (s, 3H)

EXAMPLE 25

6-Acetylamino-2-hydroxy-5,6,7,8-tetrahydro-naphthalene

Yield: 82% of theory $^1$H-NMR (CD$_3$OD): δ=2.0 (s, 3H)

EXAMPLE 26

Methyl 5-benzoylamino-5,6,7,8-tetrahydro-naphth-1-yl-oxyacetate 50 mmol of 5-benzoylamino-1-hydroxy-5,6,7,8-tetrahydro-naphthalene and 100 ml of anhydrous potassium potassium carbonate are stirred at 50° C. in 100 ml of absolute dimethylformamide for 20 minutes. A solution of 60 mmol of methyl chloroacetate and 25 mmol of potassium iodide in 25 ml dimethylformamide is added dropwise and the mixture is stirred at 50° C. for 6 to 8 hours. It is filtered under the influence of heat, the residue is rinsed thoroughly with ethyl acetate and the filtrate is evaporated. The residue is stirred in a mixture of 10% strength NaOH and ethyl acetate or tetrahydrofuran for 10 minutes. The ethyl acetate phase is extracted by shaking once with 10% strength NaOH, dried over Na$_2$SO$_4$ and evaporated. The residue is recrystallized from ethyl acetate.

Yield: 86% of theory; melting point: 242° C.

The examples of Table 2 were prepared in an analogous manner:

TABLE 2

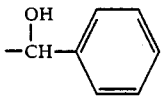

| Example No. | Substitution positions OCH$_2$CO$_2$CH$_3$ | NH—CO—R | Radical R | Yield % (in % of theory) | Melting point in the case of crystals or wave number of the amide band in the IR spectrum in the case of oils |
|---|---|---|---|---|---|
| 27 | 1 | 5 | —CH$_3$ | 92 | 196° C. |
| 28 | 1 | 5 | 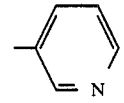 | 72 | 115° C. |
| 29 | 1 | 5 | 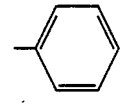 | 52 | 1665 cm$^{-1}$ |
| 30 | 2 | 5 | —CH$_3$ | 33 | 165° C. |
| 31 | 2 | 5 | 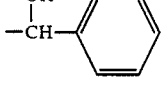 | 91 | 149–150° C. |
| 32 | 2 | 5 | 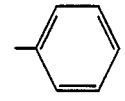 | 45 | 1665 cm$^{-1}$ |
| 33 | 1 | 6 | —CH$_3$ | 81 | 120° C. |
| 34 | 1 | 6 | 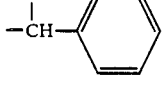 | 69 | 125–27° C. |
| 35 | 1 | 6 |  | 21 | 1670 cm$^{-1}$ |

TABLE 2-continued

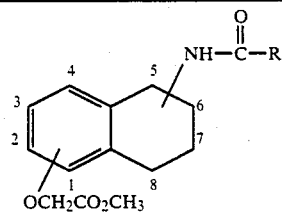

| Example No. | Substitution positions OCH₂CO₂CH₃ | NH—CO—R | Radical R | Yield % (in % of theory) | Melting point in the case of crystals or wave number of the amide band in the IR spectrum in the case of oils |
|---|---|---|---|---|---|
| 36 | 1 | 6 | 3-pyridyl | 75 | 1665 cm⁻¹ |
| 37 | 2 | 6 | —CH₃ | 82 | 110–113° C. |
| 38 | 2 | 6 | phenyl | 47 | 130° C. |
| 39 | 2 | 6 | —CH(OH)-phenyl | 14 | 1665 cm⁻¹ |
| 40 | 2 | 6 | 3-pyridyl | 44 | 1660 cm⁻¹ |

EXAMPLE 41

6-Amino-5,6,7,8-tetrahydro-naphth-1-yl-oxyacetic acid 20 mmol of methyl 6-acetylamino-5,6,7,8-tetrahydro-naphth-1-yl-oxyacetate are refluxed in 300 ml of 2N HCl for 24 hours. The product precipitates on cooling to 0° C.

Yield: 89% of theory; melting point: 271°–73° C.

The following compounds were prepared in an analogous manner:

EXAMPLE 42

5-Amino-5,6,7,8-tetrahydro-naphth-1-yl-oxyacetic acid

Yield: 17% of theory ¹H-NMR (CD₃OD): δ=4.65 (s, 2H)

EXAMPLE 43

5-Amino-5,6,7,8-tetrahydro-naphth-2-yl-oxyacetic acid

Yield: 14% of theory ¹H-NMR (CD₃OD): δ=4.65 (s, 2H)

EXAMPLE 44

6-Amino-5,6,7,8-tetrahydro-naphth-2-yl-oxyacetic acid

Yield: 71% of theory; melting point: 305° C.

EXAMPLE 45

Methyl 7,8-tetrahydro-5(6H)-naphthalenon-1-yl-oxyacetate 0.5 mol of 5-hydroxy-1-tetralone is refluxed together with 0.6 mol of methyl chloroacetate, 0.25 mol of potassium iodide and 1 mol of potassium carbonate in 1 l of butanone for 6 hours. The mixture is filtered with suction, the residue is rinsed thoroughly with acetone and the filtrate is evaporated. The residue is taken up in 500 ml of methylene chloride and the mixture is washed three times with 0.5N NaOH and once with water, dried over sodium sulphate and evaporated. The residue is distilled using a bulb tube. (Boiling point: 250° C./0.3 mm) or crystallized from ligroin (melting point: 84°–85° C.). Yield: 83% of theory The following compounds are prepared in an analogous manner:

EXAMPLE 46

Methyl 7,8-tetrahydro-5(6H)-naphthalenon-2-yl-oxyacetate

Yield: 76% of theory; melting point: 116°–118° C.

EXAMPLE 47

5-Amino-5,6,7,8-tetrahydro-naphth-1-yl-oxyacetamide 50 mmol of methyl 7,8-tetrahydro-5(6H)-naphthalenon-1-yl-oxyacetate are reacted in 100 ml of methanol and 50 ml of NH₃ for 5 hours at 110° C. under 100 bar

EXAMPLE 48

5-Amino-5,6,7,8-tetrahydro-naphth-2-yl-oxyacetamide

Yield: 89% of theory $^1$H-NMR (CD$_3$OD): $\delta$=4.45 (s, 2H)

EXAMPLE 49

5-(4-Chloro-benzenesulphonylamino)-5,6,7,8-tetrahydronaphth-2-yl-oxyacetamide 33 mmol of p-chlorosulphonyl chloride in 20 ml of absolute tetrahydrofuran are added dropwise to 30 mmol of 5-amino-5,6,7,8-tetrahydro-naphth-2-yl-oxyacetamide and 60 mmol of triethylamine in 80 ml of absolute tetrahydrofuran at room temperature. The mixture is subsequently stirred at room temperature for 6 hours and filtered and 30 ml of ether are added. The organic phase is washed with 1N HCl, saturated NaHCO$_3$ solution and saturated NaCl solution, dried over Na$_2$SO$_4$ and evaporated.

Yield: 58% of theory; $^1$H-NMR (d$_6$-DMSO): $\delta$=4.35 (s, 2H);

melting point: 203°-5° C.

EXAMPLE 50

5-(4-Chloro-benzenesulphonylamino)-5,6,7,8-tetrahydronaphth-1-yl-oxyacetamide

Yield: 52% of theory; melting point: 205°-208° C. $^1$H-NMR (d$_6$-DMSO): $\delta$=4.45 (s, 2H)

EXAMPLE 51

7-Benzenesulphonylamino-5,6,7,8-tetrahydro-1-hydroxynaphthalene 9.6 g (30 mmol) of 7-benzenesulphonylamino-1-methoxy-5,6,7,8-tetrahydronaphthalene are dissolved in 150 ml of analytical grade CH$_2$Cl$_2$, 40 ml of 1 molar (40 mmol) of boron tribromide solution are added dropwise at room temperature, the reaction mixture is subsequently stirred at room temperature for 1 hour and poured onto ice-water containing a little L-(+)-tartaric acid, the CH$_2$Cl$_2$ is separated off and the mixture is dried over MgSO$_4$ and concentrated in vacuo, crystalline residue.

Yield: 5.7 g (62.7% of theory)
Melting point: 152°-154° C.

EXAMPLE 52

Ethyl 7-benzenesulphonylamino-5,6,7,8-tetrahydronaphth-1-yl-oxyacetate 5.3 g (17.5 mmol) of 7-benzenesulphonylamino-5,6,7,8-tetrahydro-1-hydroxy-naphthalene and 2.76 g (20 mmol) of ground K$_2$CO$_3$ are stirred in 100 ml of analytical grade dimethylformamide, 3.35 g (20 mmol) of ethyl bromoacetate are added dropwise at room temperature the reaction mixture is subsequently stirred at room temperature for 1 hour and filtered and the mother liquor is concentrated in vacuo.

Yield: 6.6 g (97% of theory)
Rf value: K$_{60}$ film 0.45 (mobile phase toluene: acetone 4:1)

EXAMPLE 53

7-Benzenesulphonylamino-5,6,7,8-tetrahydronaphth-1-yl-oxyacetic acid 3.89 g (10 mmol) of ethyl 7-benzenesulphonylamino-5,6,7,8-tetrahydronaphth-1-yl-oxyacetate and 840 mg (15 mmol) of KOH are stirred in 50 ml of C$_2$H$_5$OH and 20 ml of H$_2$O at room temperature for 20 hours. The solvent is stripped off, the residue is partitioned between H$_2$O and CH$_2$Cl$_2$, the mixture is brought to pH 4.5 with 10% strength HCl and extracted twice with CH$_2$Cl$_2$, the organic phases are dried over MgSO$_4$ and concentrated in vacuo, the residue is triturated with ether and the crystals are filtered off with suction and dried.

Yield: 1.8 g (49.7% of theory)
Melting point: 205° C.

EXAMPLE 54

6-Benzenesulphonylamino-5,6,7,8-tetrahydro-naphth-1-yl-oxyacetic acid 10 mmol of 6-amino-5,6,7,8-tetrahydro-naphth-1-yl-oxyacetic acid and 20 mmol of benzenesulphonyl chloride are warmed at 80° C. in 40 ml of 10% strength NaOH for 2 hours. The mixture is then acidified with concentrated HCl and the milky suspension is extracted by shaking twice with ethyl acetate. The combined ethyl acetate phases are rapidly extracted by shaking with 10% strength NaOH (product precipitates out of the ethyl acetate), the NaOH phase is acidified with concentrated HCl and extracted by shaking twice with ethyl acetate and the extract is dried over Na$_2$SO$_4$ and evaporated. The residue is boiled up in ethyl acetate and the mixture is filtered. The product crystallizes out after 2-3 hours in a refrigerator.

Yield 63% of theory $^1$H-NMR (NaOD): $\delta$=4.55 (s, 2H), melting point: 175° C.

The following compounds were prepared analogously:

EXAMPLE 55

6-(4-Chlorobenzenesulphonylamino)-5,6,7,8-tetrahydronaphth-1-yl-oxyacetic acid

Yield: 67% of theory; melting point: 248° C.

EXAMPLE 56

6-Benzenesulphonylamino-5,6,7,8-tetrahydro-naphth-2-yl-oxyacetic acid

Yield: 54% of theory $^1$H-NMR (NaOD): $\delta$=4.5 (s, 2H)

EXAMPLE 57

5-(4-Chlorobenzenesulphonylamino)-5,6,7,8-tetrahydronaphth-2-yl-oxyacetic acid 10 mmol of 5-(4-chlorobenzenesulphonylamino)-5,6,7,8-tetrahydro-naphth-2-yl-oxyacetamide are heated under reflux in 12 ml of 2N KOH and 40 ml of MeOH for 6 hours. The methanol is stripped off, 30 ml of 1N KOH are added and the mixture is extracted by shaking twice with CH$_2$Cl$_2$. The H$_2$O phase is brought to pH 2 with concentrated HCl and the precipitate is filtered off and dried thoroughly.

Yield: 71% of theory
$^1$H-NMR (d$_6$-DMSO): $\delta$=4.6 (s, 2H)

The following compounds are prepared analogously:

EXAMPLE 58

5-(4-Chlorobenzenesulphonylamino)-5,6,7,8-tetrahydronaphth-1-yl-oxyacetic acid

Yield: 66% of theory; melting point: 210° C. (ethyl acetate/petroleum ether)

EXAMPLE 59

5-(4-Fluorobenzenesulphonylamino)-5,6,7,8-tetrahydronaphth-1-yl-oxyacetic acid

Yield: 68% of theory; melting point:

EXAMPLE 60

5-Benzoylamino-5,6,7,8-tetrahydro-naphth-1-yl-oxyacetic acid 50 mmol of methyl 5-benzoylamino-5,6,7,8-tetrahydro-naphth-1-yl-oxyacetate are stirred in 60 ml of 1N NaOH and 120 ml of MeOH at room temperature for 6 hours. The methanol is stripped off, the NaOH solution is extracted by shaking with ethyl acetate and the extract is then acidified with 10% strength HCl solution. The acid solution is extracted by shaking 3 times with ethyl acetate or tetrahydrofuran, the extract is dried over $Na_2SO_4$ and evaporated and the residue is dried under a high vacuum.

Yield: 94% of theory; IR: 1745 cm$^{-1}$ (CO$_2$H)

Further examples which were prepared in an analogous manner are summarized in Table 3:

TABLE 3

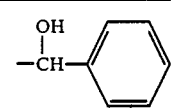

| Example No. | Substitution positions OCH$_2$CO$_2$H | NH—CO—R | Radical R | Yield % (in % of theory) | Wave number of the carbonyl band in the IR spectrum |
|---|---|---|---|---|---|
| 61 | 1 | 5 | 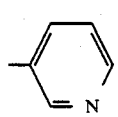 | 91 | 1735 cm$^{-1}$ |
| 62 | 1 | 5 | 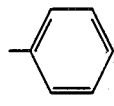 | 87 | 1730 cm$^{-1}$ |
| 63 | 2 | 5 | 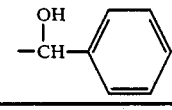 | 90 | 1755 cm$^{-1}$ |
| 64 | 2 | 5 | 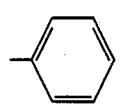 | 92 | 1725 cm$^{-1}$ |

| Example No. | Substitution positions OCH$_2$CO$_2$H | NH—CO—R | Radical R | Yield % (in % of theory) | wave number of the amide band in the IR spectrum in the case of oils |
|---|---|---|---|---|---|
| 65 | 1 | 6 | 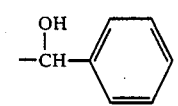 | 96 | 1745 cm$^{-1}$ |
| 66 | 1 | 6 | 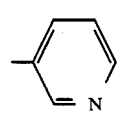 | 94 | 1740 cm$^{-1}$ |
| 67 | 1 | 6 |  | 89 | 1730 cm$^{-1}$ |

TABLE 3-continued

[Structure: tetrahydronaphthalene with NH-C(=O)-R at position 5, and OCH₂CO₂H at position 1; positions labeled 1-8]

| No. | | | R | Yield (%) | IR |
|---|---|---|---|---|---|
| 68 | 2 | 6 | phenyl | 95 | 1725 cm$^{-1}$ |
| 69 | 2 | 6 | -CH(OH)-phenyl | 95 | 1725 cm$^{-1}$ |
| 70 | 2 | 6 | 3-pyridyl | 89 | 1725 cm$^{-1}$ (m.p. 211° C.) |

It will be understood that the specification and examples are illustrative but not limitative of the present invention and that other embodiments within the spirit and scope of the invention will suggest themselves to those skilled in the art.

What is claimed is:

1. A compound of the formula

[Structure: 2-amino-tetrahydronaphthalene with OCH₂COR² substituent]

R² represents OH, alkoxy, phenoxy, benzoxy or NR⁵R⁶, wherein

R⁵ and R⁶ are identical or different and each represents hydrogen or alkyl, or one of the radicals R⁵ or R⁶ represents benzyl.

* * * * *